United States Patent [19]

Manning

[11] Patent Number: 5,678,570
[45] Date of Patent: Oct. 21, 1997

[54] METHOD OF TREATING CARDIAC ARREST

[75] Inventor: James E. Manning, Chapel Hill, N.C.

[73] Assignee: The University of North Carolina at Chapel Hill, Chapel Hill, N.C.

[21] Appl. No.: 422,337

[22] Filed: Apr. 14, 1995

[51] Int. Cl.$^6$ .................................................. A61B 19/00
[52] U.S. Cl. ................... 128/897; 600/16; 604/4
[58] Field of Search ............... 600/16–18; 128/897–898; 606/194; 604/23, 28, 49, 51, 56, 96, 97, 4

[56] References Cited

U.S. PATENT DOCUMENTS

| | | | |
|---|---|---|---|
| 3,962,439 | 6/1976 | Yokoyama et al. | 424/248 |
| 4,686,085 | 8/1987 | Osterholm | 422/45 |
| 5,085,630 | 2/1992 | Osterholm et al. | 604/28 |
| 5,216,032 | 6/1993 | Manning | 514/718 |
| 5,334,142 | 8/1994 | Paradis | 604/53 |
| 5,449,342 | 9/1995 | Hirose et al. | 600/16 |
| 5,494,905 | 2/1996 | Karcher et al. | |

FOREIGN PATENT DOCUMENTS

1076119 A   2/1984   U.S.S.R. .

OTHER PUBLICATIONS

H. Memezawa et al., Effects of Fluosol–DA on Brain Edema, Energy Metabolites, and Tissue Oxygen Content in Acute Cerebral Ischemia, *Advances in Neurology*, vol. 52, pp. 109–117 (1990).

Emerman, et al., Hemodynamic Effects of the Intra–aortic Balloon Pump During Experimental Cardiac Arrest, *Am. J. Emerg. Med.*, vol. 7, pp. 378–383 (1989).

Clemann, et al., Prevention of ischemia during percutandous transluminal coronary angioplasty by transcatheter infusion of oxygenated Flusol DA 20%, *Circulation*, vol. 74 (1986).

Becker, et al., Outcome of CPR in a Large Metropolitan Area—Where are the Survivors?, *Animals of Emergency Medicine*, pp. 355–361, (1991).

Bajaj, et al., Limitation of Myocardial Reperfusion Injury by Intravenous Perfluorochemicals, *Circulation*, vol. 79, pp. 645–656 (1989).

*The Merck Index; An Encyclopedia of Chemicals, Drugs, and Biologicals*, pp. 392, 625, 933, 1131 (1989).

Martin, et al., Aortic and Right Atrial Pressures During Standard and Simultaneous Compression and Ventilation CPR in Human Beings, pp. 125–130, (1986).

Hoffman et al., Digitalis and Allied Cardiac Glycosides, *Goodman and Gilman's The Pharmacological Basis of Therapeutics*, pp. 716–718, (1985).

Novick, et al., Protection of the hypertrophied pig myocardium, *Cardiovasc Surg*, vol. 89, pp. 547–566 (1985).

Martin et al., *Physical Pharmacy*, Third Edition, pp. 276–277, (1983).

*Primary Examiner*—John P. Lacyk
*Attorney, Agent, or Firm*—Bell, Seltzer, Park and Gibson, P.A.

[57] ABSTRACT

A method of treating a subject under cardiac arrest comprises the steps of: blocking the descending aorta of the subject; then withdrawing blood from the subject; oxygenating the blood withdrawn from the subject; and perfusing the aortic arch of the subject with oxygenated blood in an amount effective to deliver oxygen to the heart of the subject. This method enables the subject to continue to receive oxygenating material (i.e., blood in this instance) without the danger of volume overload that would be present if another oxygenated solution were continuously infused.

13 Claims, 5 Drawing Sheets

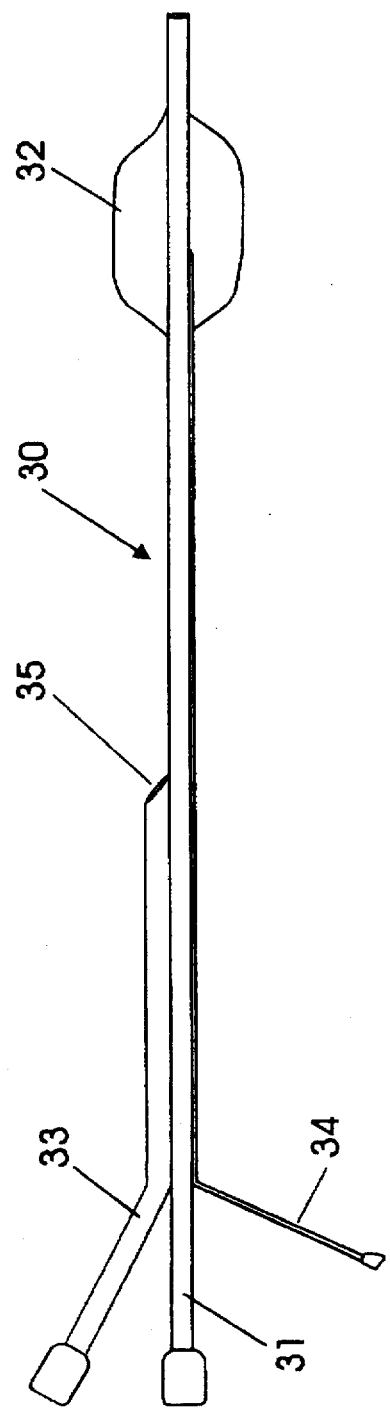
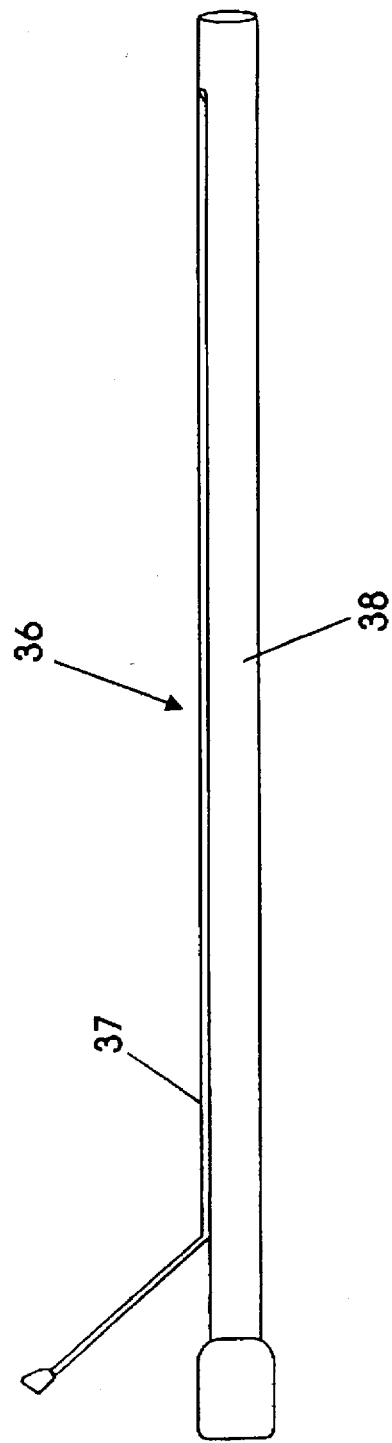

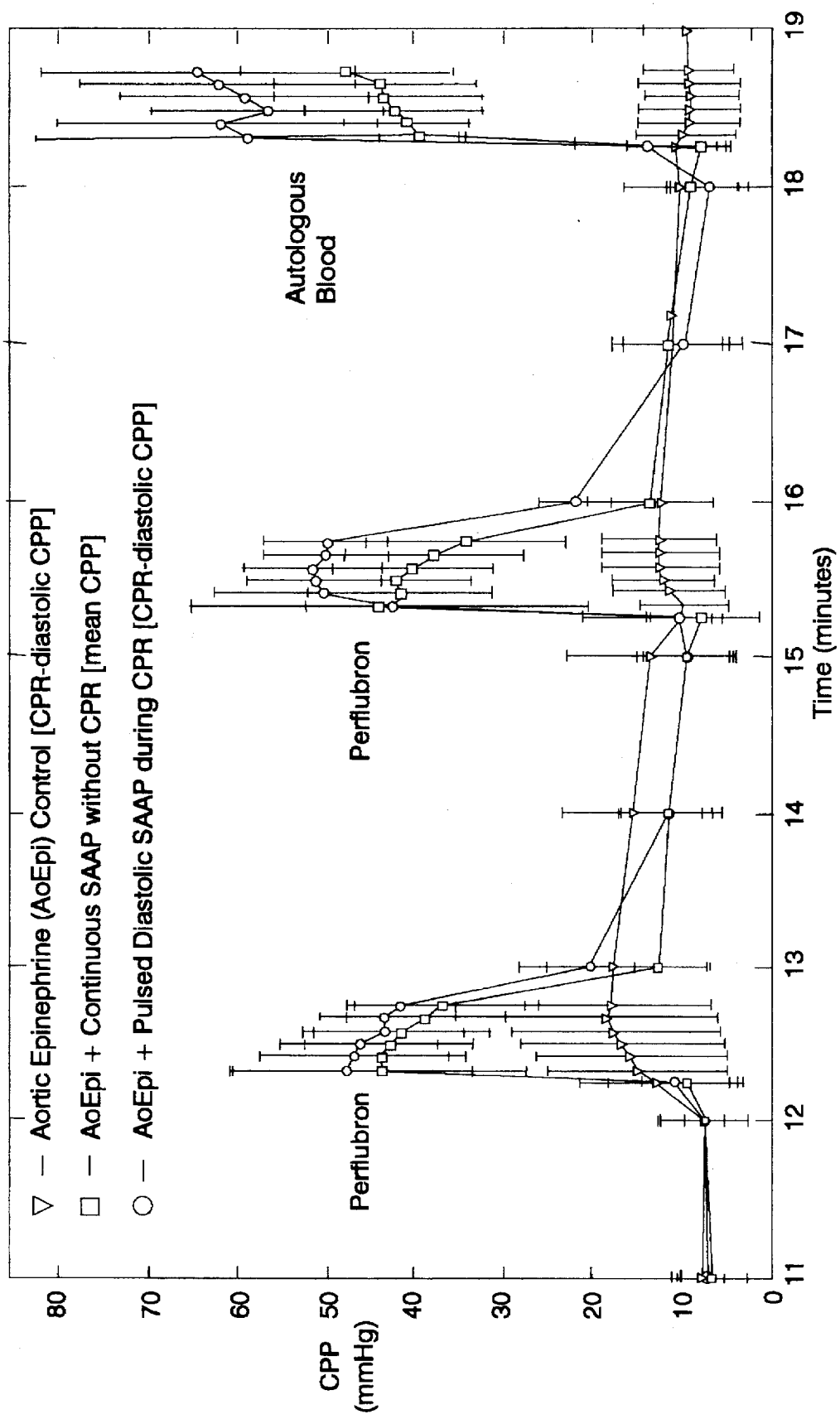

METHOD OF TREATING CARDIAC ARREST

FIELD OF THE INVENTION

The present invention relates generally to a method of treating patients in cardiac arrest, and more particularly relates to a method of treating cardiac arrest patients through selective aortic arch perfusion.

BACKGROUND OF THE INVENTION

When a person suffers a cardiac arrest, whether it be inside a hospital or elsewhere, the survival rate is relatively low. See L. Becker et al., *Ann. Emerg. Med.* 20, 355–361 (1991). One of the reasons for the high mortality rate is that cardiopulmonary resuscitation (CPR), one of the primary resuscitation methods, induces little forward blood flow. Although certain drugs, such as epinephrine, can improve vital organ blood flow during CPR, these drugs are administered almost exclusively into a vein; as such, the drug must circulate to and through the heart and lungs before arriving at the peripheral arteries where their primary beneficial pharmacological effects occur. During this low blood state of CPR, the heart and brain receive very limited blood flow blood that may fail to sustain cellular survival.

Invasive techniques such as open-chest cardiac massage (OCCM), direct mechanical ventricular assistance (DMVA), and cardiopulmonary bypass (CPB) can provide better vital organ blood flow. See generally R. Bartlett et al., *Ann. Emerg. Med.* 13(Part 2), 773–777 (1984); M. Anstadt et al., *Resuscitation* 21,7–23 (1991); P. Safar et al., *Am. J. Emerg. Med.* 8, 55–67 (1990). However, adaptation of these techniques for widespread use, particularly in a setting outside a hospital, is unrealistic. In most cases, the response time that would enable significant neurologic recovery would likely expire before these techniques could be employed in a typical emergency.

Selective aortic arch perfusion (SAAP) is a technique designed to provide relatively isolated perfusion of the heart and brain in patients suffering cardiac arrest. SAAP is typically performed by inserting a large lumen balloon occlusion catheter, percutaneously or by surgical cutdown, into a femoral artery and then advancing the catheter tip to the descending aortic arch, preferably just distal to the left subclavian artery. With the SAAP catheter balloon inflated to prevent or restrict distal aortic flow, the coronary and cerebral circulations can be relatively selectively perfused with a solution infused via the lumen of the SAAP catheter. The infused solution is typically an oxygenated blood substitute, such as a perfluoro carbon emulsion or polymerized hemoglobin solution, that contains various agents capable of reversing ischemic metabolic processes, restoring peripheral vascular resistance, correcting hemostatic derangements, and limiting reperfusion-induced cellular damage. For example, vasoconstrictors such as epinephrine are beneficial. Perfusion with such a solution can enhance return of spontaneous cardiac function and facilitate neuronal functional recovery. This technique is described in some detail in U.S. Pat. No. 5,216,032 to Manning.

Although research indicates that SAAP shows promise, the technique has certain shortcomings. SAAP is a volume loading procedure and, as such, is volume limiting. When excess volumes of protective solution are infused, as may happen if an initial SAAP infusion is insufficient to resuscitate the patient and is followed by subsequent infusions, pulmonary congestion and edema can result, each of which can have a significant adverse effect on pulmonary oxygenation. The prior art is silent regarding methods of avoiding volume overload during SAAP.

SUMMARY OF THE INVENTION

The present invention addresses this shortcoming. The present invention includes as a first aspect a method of treating a subject under cardiac arrest which comprises the steps of: blocking the descending aorta of the subject; then withdrawing autologous blood from the subject; oxygenating the autologous blood withdrawn from the subject; and perfusing the aortic arch of the subject with the oxygenated autologous blood in an amount effective to deliver oxygen to the heart of the subject. This method enables the subject to continue to receive oxygenated material (i.e., blood in this instance) without the danger of volume overload that would be present if another oxygenated solution, such as a blood substitute or heterologous blood, were continuously infused. It is preferred that an anticoagulant be administered to the autologous blood after withdrawal and before oxygenation, and it is also preferred that perfusion with autologous blood follow one or more perfusions with a heterologous protective solution, such as a blood substitute. The autologous blood can be withdrawn from a vein, such as the femoral vein, or from the aorta itself.

As a second aspect, the present invention includes an apparatus for treating a subject in cardiac arrest. The apparatus comprises: means for perfusing the aorta of the subject with a heterologous protective solution; means for withdrawing autologous blood from the subject; means for oxygenating the autologous blood; and means for perfusing the aorta of the subject with the oxygenated autologous blood. Preferably, the apparatus further comprises means for introducing anticoagulant into the autologous blood. It is also preferred that the means for perfusing the aorta with heterologous protective solution and the means for perfusing the aorta with autologous blood comprises a shared catheter having a common outlet.

BRIEF DESCRIPTION OF THE DRAWINGS

FIG. 3 is a schematic illustration of a triple lumen balloon catheter having a blood withdrawal line configured to withdraw blood from the distal aorta.

FIG. 4 is a schematic representation of a blood withdrawal catheter having an anticoagulant infusion port.

FIG. 6 is a graph plotting coronary perfusion pressure as a function of time for a control group of animals that received only epinephrine, an experimental group that received both epinephrine and continuous SAAP, and an experimental group that received epinephrine and pulsed diastolic SAAP.

DETAILED DESCRIPTION OF THE INVENTION

The present invention will now be described hereinafter in detail with reference to the accompanying drawings. The present invention is not, however, limited to the embodiments described herein; rather, these embodiments are intended to enable those skilled in this art to understand fully the invention.

As described above, the present invention is directed to methods and associated apparatus for treating a subject in cardiac arrest. As used herein, the term "cardiac arrest" refers to all types of cardiac arrest, including ventricular fibrillation, asystole, and pulseless electrical activity. The subject of such cardiac arrest is preferably mammalian and more preferably human, but can be any animal that can be advantageously treated by oxygenating its brain and coronary vasculature during cardiac arrest.

Figure 1:
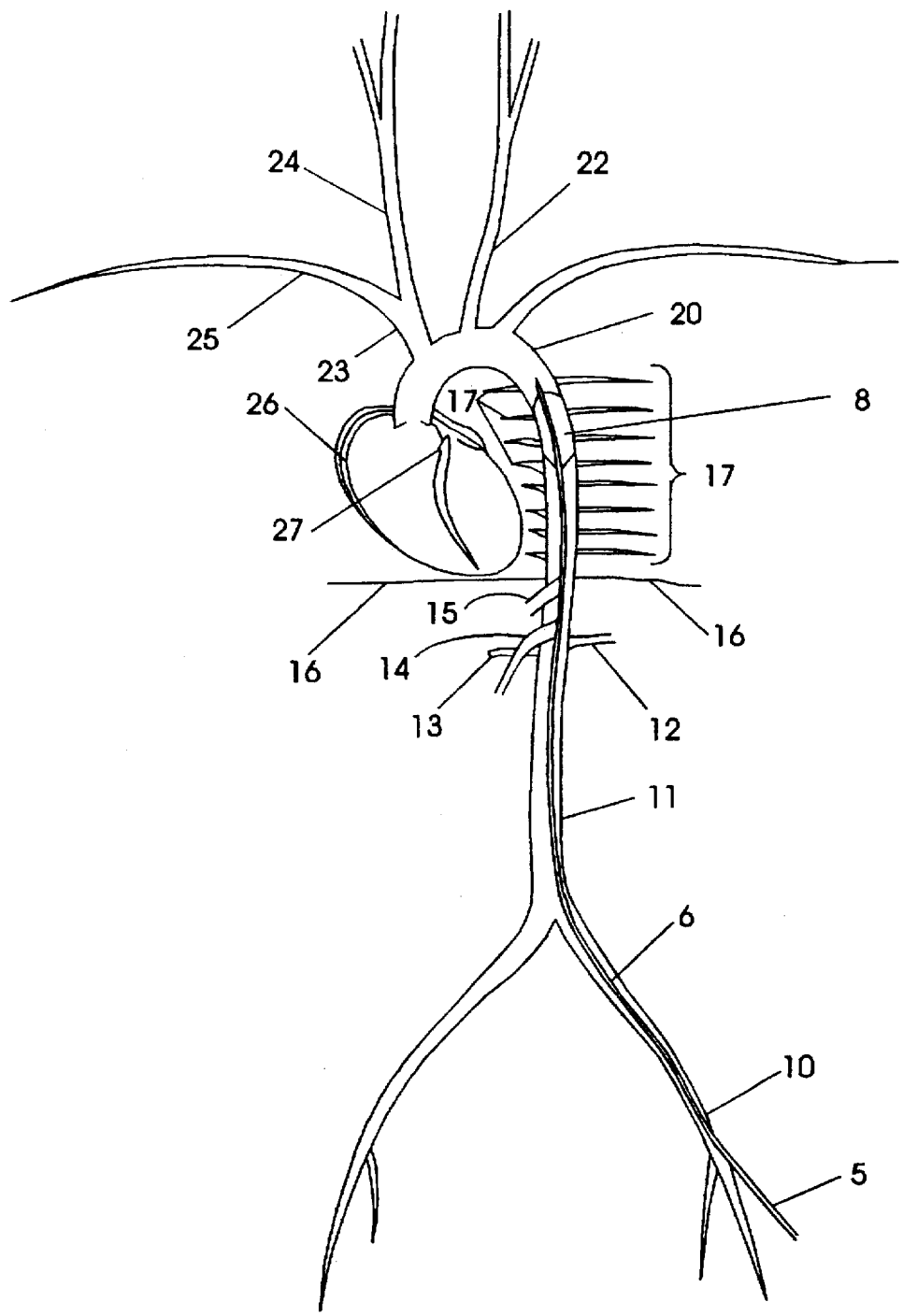
FIG. 1 is a schematic illustration of a balloon catheter inserted through the femoral artery into the aorta in a human subject proximal to the diaphragm but distal to the left subclavian artery, with the balloon inflated to block the descending aorta.

Blocking of the descending aorta, and infusion into the aortic arch, is preferably carried out with a balloon catheter unit such as that illustrated at 5 in FIG. 1. The balloon catheter unit 5 comprises an elongate catheter tube 6 having a primary lumen 7 through which protective solution may pass, and further comprises a balloon 8 at one end of the elongate tube 6 configured to be inflated to block the descending aorta of a human subject. A secondary tube 9 (or alternatively a secondary lumen formed in the wall of the tube 6 and extending longitudinally therewith) provides a mechanism for inflating the balloon 8 once the balloon 8 is positioned in the desired location within the descending aorta of the subject. A connector such as a Leur Lock™ fitting is provided at the end of the elongate tube 6 opposite the balloon 8 to connect the catheter tube 6 to a supply for the protective solution.

For a human adult, the size of the primary lumen 7 may be from 6 French to 14 French, the length of the catheter tube 6 may be from 50 to 150 centimeters, the inflated dimensions of the balloon 8 may be from 1.5 to 4 centimeters in diameter, the length of the balloon 8 may be from 2 to 10 centimeters, and the distance from the tip of the catheter tube 6 to the balloon 8 distance may be from 1 to 4 centimeters. For a human child, the lumen size may be from 5 French to 10 French, the catheter tube length may be from 20 to 80 cm, the balloon inflated dimensions may be from 0.75 to 2 cm in diameter, the balloon length may be 1.5 to 6 cm, and the catheter-tip to balloon distance may be from 0.5 to 2 cm. When inflated, the balloon 5 should be capable of withstanding a pressure of at least 300 to 500 mmHg to prevent leakage of protective solution down the descending aorta and rupture of the balloon during chest compression.

The catheter tube 6 may be made from a firm but somewhat flexible plastic material, and the balloon 8 from a latex or polyurethane material. The catheter tube 6 may be made from antithrombotic materials, such as having heparin bonding as a characteristic of construction, to inhibit formation of blood clots in the aorta. Reference may be made to U.S. Pat. Nos. 5,049,132; 5,049,131; 5,045,061; 5,042,976; 5,041,125; and 5,216,032 for further guidance in the construction of the balloon catheter. It is specifically intended that the disclosures of all patent references cited herein be incorporated herein by reference.

Figure 2:
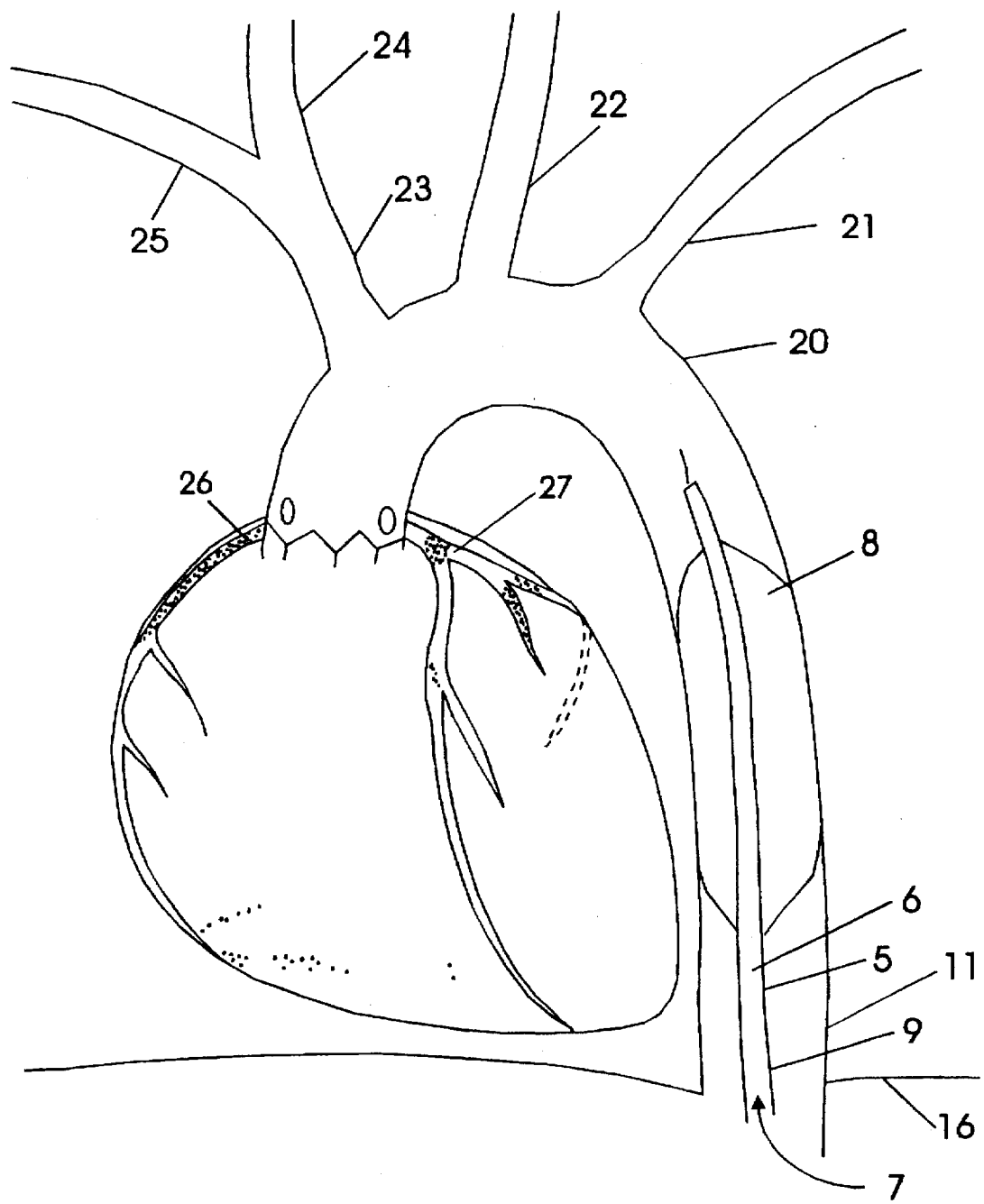
FIG. 2 is an enlarged partial view of the heart and balloon catheter of FIG. 1 showing the balloon catheter positioned to block the descending aorta and perfuse the aortic arch.
Figure 5:
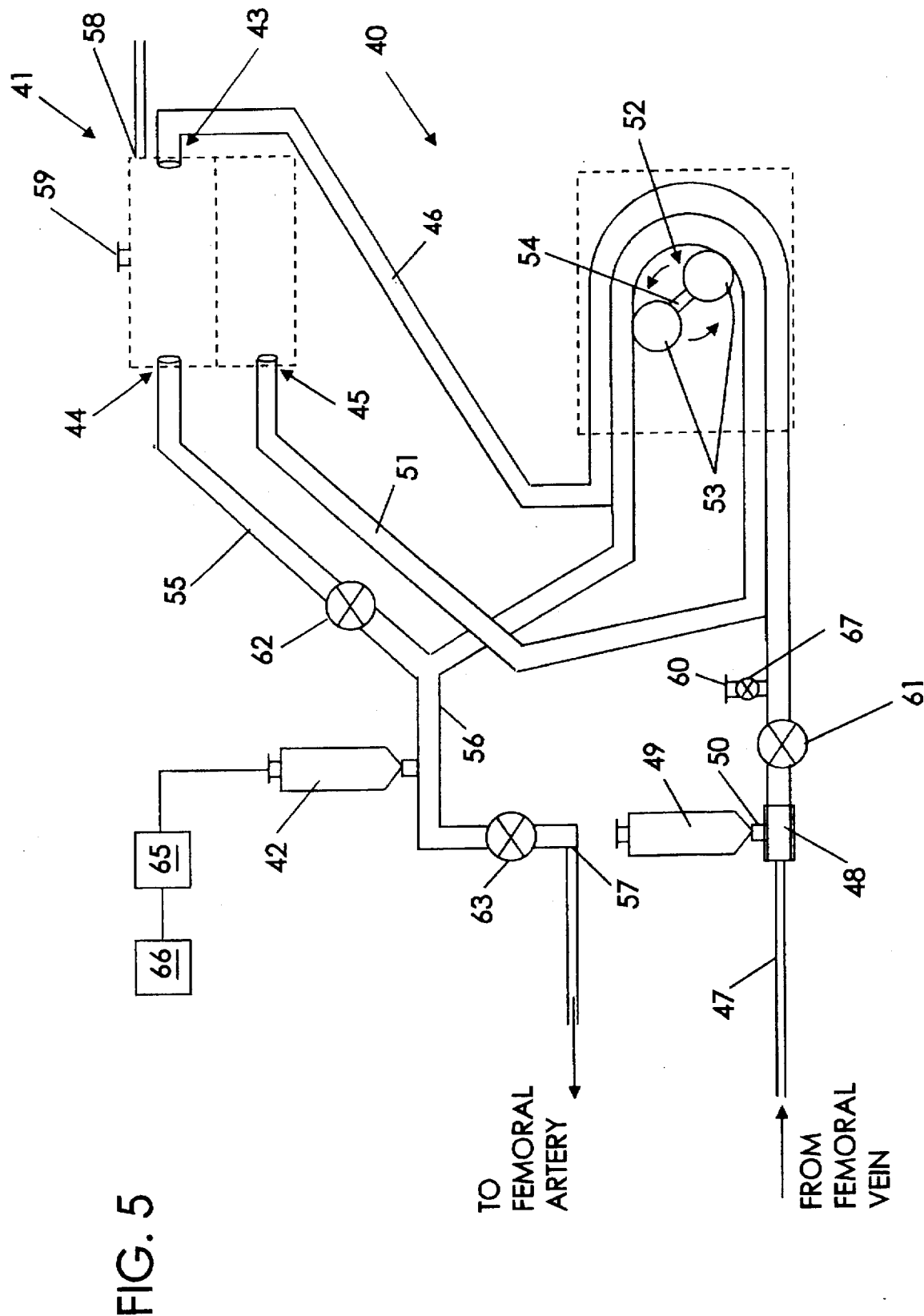
FIG. 5 is a schematic illustration of an exemplary SAAP system and its catheter extending into the femoral artery of a subject.

To block the descending aorta of the subject (FIGS. 1 and 2), the balloon catheter unit 5 is inserted into a femoral artery 10 of the subject and advanced within the descending aorta 11 past the renal arteries 12, 13, the superior mesenteric artery 14, the celiac trunk 15, the diaphragm 16, and past various ones of the intercostal arteries 17. The balloon 8 is preferably positioned distal to the carotid arteries 22, 24 and the left subclavian artery 21, but is preferably located at least proximal to the renal arteries 12, 13. The balloon 8 is inflated via the secondary tube 9 to block the descending aorta 11, with the leading end of the elongate tube 6 positioned to perfuse the aortic arch 20. In this position, protective solution pumped or forced through the balloon catheter unit 5 and exiting the balloon 8 will perfuse the left subclavian artery 21, the left common carotid artery 22, the brachiocephalic trunk 23 (and in turn the right carotid artery 24 and the right subclavian artery 25) and the coronary arteries 26, 27. Although it is preferred to block the descending aorta with a balloon catheter as illustrated, those skilled in this art will appreciate that other means for blocking the descending aorta to prevent flow therein can also be used with the present invention.

Withdrawing the subject's blood can be carried out in any manner known to those skilled in this art to be suitable therefor. One technique of withdrawing autologous blood from the subject is to insert a catheter into the femoral vein (or some other large vein, such as the jugular vein or subclavian vein). This technique would allow blood to be continuously withdrawn and infused. Another technique would be to withdraw the blood from the proximal aorta with the balloon of the balloon catheter deflated. An alternative technique would involve withdrawing blood from the distal aorta with the balloon inflated, which may be preferred due to the capability of continuous infusion and withdrawal. A catheter embodiment for such withdrawal is illustrated schematically in FIG. 3. A balloon catheter unit 30 comprises two large lumens: an infusion lumen 31 that terminates beyond the balloon 32; and a blood withdrawal lumen 33 that terminates prior to the balloon 32. A balloon inflation line 34 terminates within the balloon 32. This embodiment enables blood to be withdrawn into the blood withdrawal lumen 33 either when the balloon 32 is deflated or inflated when the inlet 35 of the blood withdrawal lumen 33 is positioned in the distal aorta.

Once blood is withdrawn from the subject, it is preferably mixed with an anticoagulant to keep the blood from coagulating. Exemplary anticoagulants include heparin, acid citrate dextrose, or sodium citrate. Typically, the anticoagulant is simply added via a syringe to a conduit containing the withdrawn blood. Alternatively, anticoagulant can be added within a withdrawing catheter prior to the blood actually exiting the subject. A catheter configured for such use, designated at 36, is illustrated schematically in FIG. 4. An anticoagulant infusion line 37 terminates within and near the end of the blood withdrawal lumen 38. This catheter configuration enables anticoagulant to be introduced into the blood as the blood enters the catheter, and thus can reduce the degree of coagulation experienced by that blood. This catheter configuration can be combined with that described above in FIG. 3 to enable blood withdrawn from the distal aorta to receive anticoagulant just as it leaves the bloodstream.

After withdrawal, the blood is then oxygenated. Oxygenation can be performed in any manner known to those skilled in this art to oxygenate blood. For example, blood can be shunted into a tank or reservoir having an oxygen membrane and passed therethrough.

It is preferred that the withdrawn blood be passed through a filter or other device that removes any blood clots or other debris prior to reinfusion, as such debris can adversely affect perfusion.

Once the blood is oxygenated, it can be infused into the aorta of the subject. Typically between about 250 to 3000 milliliters of the blood are infused, with 750 to 2000 milliliters of the blood being a more preferred dosage. Perfusion should be carried out sufficiently rapidly to enhance cardiac electrical activity; preferably, the perfusion duration is less than five minutes, and more preferably is less than one to two minutes. In general, the rate of infusion will be from 5 to 20 mL/kg/minute, and will most preferably be from 10 to 15 mL/kg/minute.

Perfusion of the newly-oxygenated blood can be carried out continuously, or preferably can be carried out in a pulsatile rhythm. Perfusion with a pulsatile rhythm can assist in removing sludged blood cells from the microvasculature of the subject and may have positive effects on resuscitation due to the rheology of blood. In particular, perfusion with a pulsatile rhythm in which the perfusion "pulses" are timed to coincide with the decompression or relaxation phases of CPR (diastolic pulsing) can be especially effective. See co-pending U.S. patent application entitled METHOD OF TREATING CARDIAC ARREST AND APPARATUS FOR TREATING SAME, filed concurrently, for a detailed discussion of pulsatile perfusion.

A vasoconstrictor may be employed in the methods described herein. Exemplary adrenergic vasoconstrictors include epinephrine, norepinephrine, methoxamine, phenylephrine, with epinephrine being preferred; nonadrenergic vasoconstrictors can also be used. Vasoconstrictors may be administered by any suitable means, such as by parenteral injection (e.g., intravenous injection, intraarterial injection, subcutaneous injection, intramuscular injection, intraperitoneal injection, tracheobronchial administration), or by including the vasoconstrictor in the protective solution used to perfuse the aortic arch. It is preferred that the administration of the vasoconstrictor be concurrent with (i.e., sufficiently close in time to) perfusion of the aortic arch so that the vasoconstrictor will affect coronary perfusion with the autologous blood. The dosage of the vasoconstrictor will vary depending on the subject and the particular vasoconstrictor chosen, but will generally be between 0.002 and 0.3 mg/kg, will more preferably be between 0.005 and 0.2 mg/kg, and will most preferably be between 0.01 and 0.1 mg/kg.

Medicaments containing a vasoconstrictor for enhancing coronary perfusion with a protective solution during selective aortic arch perfusion may be prepared by contacting and mixing the vasoconstrictor with a pharmaceutically acceptable carrier, such as a sterile pyrogen-free saline solution, in accordance with techniques known in the pharmacy art. The pharmaceutical carrier may be the protective solution itself, such as a perfluorochemical blood-substitute solution as discussed above.

Restoring spontaneous circulation in the subject may be carried out by any suitable means, such as electric shock or precordial thump (i.e., application of an external force), or by enhancing electrical activity through perfusion and other resuscitation techniques so that normal electrical activity re-emerges without application of an external force. An electric shock to heart muscle tissue which will restore spontaneous circulation from a chaotic electrical signal (or "defibrillation") may be administered with any suitable defibrillator, such as the Responder™ 1500 (manufactured by Marquette Electronics, Milwaukee, Wis.).

An exemplary SAAP apparatus 40 is schematically illustrated in FIG. 3. The apparatus 40 comprises a storage tank 41 having two upper ports 43, 44, and a lower port 45. A venous blood withdrawal line 46 is attached at one end to upper port 43 and at its other end to a venous blood withdrawal catheter 47 by a fitting 48. The venous blood withdrawal catheter 47 is to be inserted into the femoral vein of a subject. An anticoagulant syringe 49 is also fluidly connected to the fitting 48 via a catheter, connector, or connector tubing 50. An oxygenated blood infusion line 51 is attached at one end to the lower port 45. As the oxygenated blood infusion line 51 extends away from the lower port 45, it meets with and travels adjacent to the venous blood withdrawal line 46. The adjacent sections of the lines 46, 51 are enclosed within a roller pump apparatus 52, which comprises a pair of wheels 53 mounted on a rotary arm 54. Rotation of the arm 54 causes the wheels 53 to contact the lines 46, 51 and thereby deliver blood or a blood substitute to and from the SAAP apparatus 40. At its outlet end, the oxygenated blood infusion line 51 meets the outlet end of an oxygenated blood recirculation line 55 that extends thereto from the upper port 44. An infusion line 56 extends from the junction of the lines 51, 55 to an infusion port 57 that is connected to the inlet end of a balloon catheter (not shown) that is to be inserted in the femoral artery of a subject. A syringe 42 is fluidly interconnected with the infusion line 56. The storage tank 41 also includes an oxygen intake port 58 and an additional syringe port 59. The venous blood withdrawal line 46 also includes an oxygen intake port 60 between the fitting 48 and the roller pump apparatus 52. Three valves 61, 62, 63 are located, respectively, adjacent the fitting 48 on the venous blood withdrawal line 46, on the oxygenated blood recirculation line 55, and on the infusion line 56 between the syringe 42 and the infusion port 57. A fourth valve 67 is located on the oxygen intake port 60. A controller 65 is operably connected with the syringe 42 to control its operation and is also operably connected with a CPR device (indicated schematically at 66). The apparatus 40 may also include a valve (not shown) that can remove any air that enters the system prior to its being introduced into the subject's aorta.

In operation, autologous blood is drawn from the subject into the femoral venous blood withdrawal catheter 47. Anticoagulant, such as heparin, is added to the withdrawn blood through the anticoagulant syringe 49. The venous blood is pumped through the venous blood withdrawal line 46 by the roller pump apparatus 52; as the rotary arm 54 rotates, the wheels 53 provide a positive pressure of the blood that forces it through the line 46. The venous blood enters the storage tank 41 through upper port 43 and flows into the bottom portion of the storage tank 41. Oxygen is continuously introduced into the storage tank through the oxygen intake port 58. After the blood is oxygenated in the storage tank 41, it flows therefrom through the lower port 45 into the oxygenated blood infusion line 51. The blood is propelled by the action of the roller pump unit 52 to the infusion line 56. Flow into the oxygenated blood recirculation line 55 is prevented because the valve 62 is in a closed position. Oxygenated blood can be furnished in a pulsatile rhythm by reciprocating action from the syringe 42. The oxygenated blood flows through the infusion line 56, through the infusion port 57, and into the SAAP catheter for delivery to the aorta.

Similarly, this apparatus 40 can also be used to deliver a blood substitute to the subject. See U.S. Pat. No. 5,216,032 to Manning for a discussion of blood substitutes. The blood substitute can be introduced into the storage tank 41 through the syringe port 59. The valves 61 and 62 are in their closed positions. The blood substitute follows the same path to the subject as that of oxygenated blood described above.

Further, the apparatus 40 can be used to recirculate, and thereby thermally and hemodynamically prepare a blood substitute for perfusion. For recirculation of blood substitute, valve 63 is in its closed position, and valve 62 is in its open position. This creates a closed loop system that proceeds from the storage tank 41 to the oxygenated blood infusion line 51, the recirculation line 55, and the upper port 44 before returning to the storage tank 41.

Use of the apparatus 40 is exemplified by the following scenario. A physician arrives at the scene of a cardiac arrest patient and secures access to the femoral artery by either percutaneous or surgical means. The blood substitute is oxygenated during the vascular access procedure. The catheter is advanced to the thoracic aorta and epinephrine is administered into the aortic arch. The catheter balloon is inflated and an initial SAAP infusion of the blood substitute (which can contain reperfusion-injury combating agents) is performed. An initial bolus of blood substitute is rapidly infused to close the aortic valve and CPR is halted for the initial infusion lasting 30 to 60 seconds. This would assure that the myocardium was effectively perfused with the blood substitute. During this initial infusion, access to a femoral vein is secured. Aortic arch epinephrine administration can be titrated to maximize CPR-diastolic coronary perfusion pressure (CPP). Two to three minutes after the initiation of the first blood substitute infusion, a second blood substitute infusion is initiated. Pulsed diastolic infusion induced by the syringe 42 using half of the volume initially infused would be used to elevate CPP and diminish the volume effects of a second infusion. The infusion pulses are administered during the decompression and relaxation phases of CPR. During the second blood substitute infusion, femoral blood is withdrawn, anticoagulated via the anticoagulant syringe, oxygenated in the storage tank 41, thermally treated (if necessary), and filtered in preparation for reinfusion. Depending upon the rapidity of femoral venous access and blood withdrawal, either a third blood substitute infusion similar to the second or an autologous blood infusion is initiated. Aortic arch epinephrine titration, other pharmacologic therapies, and repetitive or continuous autologous blood SAAP can be performed until return of spontaneous circulation (ROSC) is attained or the resuscitative efforts are halted. If ROSC is attained, autologous blood withdrawal and reinfusion could be continued (with or without the catheter balloon inflated depending on the clinical situation) serving as partial cardiopulmonary bypass support for the still unstable cardiovascular system in the early post-resuscitation phase. Graded balloon inflation could be used to provide peripheral resistance as needed in the immediate and early post-resuscitation phase.

In view of the considerable out-of-hospital use anticipated with the present invention, it is preferred that the SAAP apparatus be packaged to be easily portable. The apparatus can be packaged in a suitcase, attache case, backpack, or the like, and be easily carried to the patient for use by a physician or paramedic.

The present invention may be beneficial in the management of traumatic and other nontraumatic/surgical causes of cardiac arrest or profound hypovolemia with impending cardiac arrest. In addition to rapid volume replacement, the catheter balloon could serve much like an aortic cross-clamp to significantly reduce or stop exsanguinating hemorrhage from the abdomen, pelvis, or lower extremities until the patient could be transferred to the operating room. Clinical situations where the present invention can be used include: blunt abdominal or multi-system trauma with profound hemorrhage/hypovolemia; penetrating abdominal trauma with profound hemorrhage/hypovolemia; ruptured abdominal aortic aneurysm with profound hypotension or impending arrest; and major pelvis fractures or disruption. In hemorrhagic/hypovolemic conditions, heterologous human blood, such as from a blood bank, may also be employed.

The invention is disclosed in greater detail in the following non-limiting examples. In the examples, "kg" means kilograms, "mg" means milligrams, "mmHg" means pressure measured in millimeters of mercury, "°C." means degrees Celsius, "Fr" means lumen diameter measured in French, "mL" means milliliters, "mEq" means milliequivalents, "Hz" means Hertz, "cm" means centimeters, "J" means joules, "min" means minutes, "sec" means seconds, and "w/v" means weight per unit volume.

EXAMPLE 1

Animal Model of Cardiac Arrest

The canine cardiac arrest model described in this section was used for all of the SAAP studies subsequently described. Differences in the protocols between experimental studies are described under the individual study sections.

Animals:

Mongrel canines from a single provider source were used in all of the SAAP studies. Animals were evaluated by the staff of the Division of Laboratory Animal Medicine for evidence of acute or chronic illness.

Anesthesia:

Anesthesia was induced with thiopental 25–30 mg/kg IV and maintained with inhalational enflurane at 1.5% using a volume ventilator at an $F_1O_2$ of 0.21. End-tidal $CO_2$ was continuously measured with a sidestream sampling capnometer (Datex) and minute ventilation was adjusted to an end-tidal $CO_2$ of 38–42 mmHg. ECG lead II was monitored. Body temperature was maintained at 37°–38° C. with a warming blanket. Arterial blood gases were obtained to assure normal acid-base status. Ventilatory adjustments were made as needed to adjust the arterial pH to the 7.30–7.40 range. Serial evaluation of reflexes, heart rate and responses to graded pain stimulation were performed to assure adequate anesthesia.

Instrumentation:

Catheter introducers (8.5 Fr) were placed percutaneously into the right and left external jugular veins. Surgical cutdowns were performed to expose the right and left femoral vessels. Fluoroscopy was used to position all catheters. A Swan-Ganz catheter and a pacing wire were inserted via the external jugular veins into a pulmonary artery and the right ventricle, respectively. Micromanometer-tipped catheters (Millar Instruments) were positioned via the right femoral vessels into the right atrium and mid-aortic arch. A 9 Fr balloon occlusion catheter was inserted into the left femoral artery and advanced to the descending aortic arch. A 9 Fr catheter introducer was placed in the left femoral vein in animals undergoing blood withdrawal for subsequent reinfusion. A low pressure saline-filled balloon catheter was placed in the retrocardiac esophagus with a micromanometer catheter inside the balloon to measure esophageal pressure. Esophageal pressure served as an extravascular indicator of intrathoracic pressure changes during CPR. ECG and all pressures were continuously recorded on a multi-channel analog recorder (Grass Instruments Model 7 Polygraph).

Selective Aortic Arch Perfusion System:

The major components of the SAAP system were: (1) a 9 Fr aortic arch balloon occlusion catheter; (2) a resuscitation solution; (3) an infusion pump; and (4) an oxygenation apparatus. Perfluorooctyl bromide emulsion (perflubron emulsion, [Oxygent™, Alliance Pharmaceutical Corporation, San Diego]) in a 60% weight/volume preparation was the resuscitation solution used in all studies evaluating pulsatile SAAP. Autologous blood was withdrawn and reinfused by the SAAP technique after initial perflubron infusion in the procedure described in Example 3 and as the only SAAP perfusate in the procedure described in Example 2. The infusion pump used was a Sarns low-pressure bypass pumphead. Pulsed infusion during SAAP was created using a 50 ml syringe connected to the infusion tubing between the Sarns pump and the SAAP catheter. The syringe was cyclically filled and emptied manually with approximately 10 ml of infusate withdrawn and then infused under maximal manual pressure at a rate of 60–80 pulsed infusions per minute. During the syringe withdrawal phase, all infusate from the Sarns pump was directed into the 50 ml syringe and, therefore, essentially no infusion through the SAAP catheter occurred during this phase. During the syringe emptying (infusion) phase, perfusate from both the syringe and the pump were permitted to flow out of the SAAP catheter. The total volume infused per infusion pulse was approximately 10 ml.

Perflubron emulsion was oxygenated with 100% oxygen to yield a $pO_2$ in the range of 730–790 mmHg. Sodium bicarbonate 3.0–4.0 mEq was added to each 300 ml volume of 60% w/v perflubron emulsion in order to yield a pH of 7.35–7.45. The $pCO_2$ with this preparation was less than 10 mmHg. Temperature was adjusted to 37° C.

In the two procedures using autologous blood (Examples 2 and 3), femoral venous blood was withdrawn, heparinized, circulated through the oxygenator, maintained at 37° C. and then reinfused via the SAAP catheter at time intervals described in the individual study sections.

The SAAP catheter latex balloon was inflated sufficiently to completely occlude the aorta just prior to SAAP infusion and the Sarns pump was used to infuse the perflubron and/or autologous blood. For all SAAP infusions used in the SAAP studies, an initial 50 ml bolus was rapidly infused in order to competently close the aortic valve. After the initial bolus, an infusion was maintained using the SARNS low-pressure bypass pumphead for a prescribed time interval.

Protocol—Baseline measurements of heart rate, aortic pressure, right atrial pressure, cardiac output, hematocrit, respiratory rate, tidal volume, end-tidal $CO_2$ arterial blood gases, and mixed venous blood gases were obtained before cardiac arrest. Ventricular fibrillation was induced using alternating current (60 Hz) applied to the heart for 3–5 seconds via the right ventricular pacing wire. Ventilatory support simultaneously ceased and the animals remained in ventricular fibrillation and total circulatory arrest for ten minutes. At the ten minute mark, mechanical CPR (Thumper™, Michigan Instruments) was initiated at a rate of 80 compressions of 130 lb per minute with animals in the supine position. Unless otherwise indicated, CPR was accompanied by epinephrine dosages of 0.01 mg/kg given intravenously. Ventilation was performed using 100% $O_2$ and inspiratory force of 25 cm $H_2O$ at a 5:1 compression-:ventilation ratio.

Experimental Therapeutic Interventions—Experimental interventions were initiated at 12 minutes after arrest. In all of the SAAP studies, defibrillation (electrical countershock) was attempted at one minute intervals as indicated after the experimental interventions were begun; defibrillation energy was applied at 100 J for the first defibrillation attempt, 150 J for the second, and 200 J for all others. Resuscitative efforts were continued as needed up to the 30 minute mark after initiation of ventricular fibrillation.

EXAMPLE 2

Serial Pulsed Diastolic SAAP-Autologous Blood Study

SAAP using only autologous blood (AB) was studied to determined if this intervention alone might improve resuscitation outcome. The pulsed CPR-diastolic SAAP infusion method was used for this study.

There were two intervention groups. The animals in the control group (n=5) received standard therapy with the exception that all epinephrine doses of 0.01 mg/kg were given at 3 min intervals via the aortic arch beginning at 12 min of arrest. The animals of the experimental group (n=5) received CPR and aortic arch epinephrine as in the control group. At the 11 min mark, left femoral venous blood withdrawal began. SAAP-PD with autologous blood began at 12 min 15 sec and was continued 45 sec while CPR was in progress. PD-AB-SAAP infusion was repeated at 2 min intervals as needed until ROSC.

The results of this procedure are shown in Table 1 below.

TABLE 1

| Group | ROSC | CPR-diastolic CPP (mmHg, mean ± S.D.) | | | | | |
|---|---|---|---|---|---|---|---|
| | | 11 min | 12 min | 13 min | 14 min | 15 min | 16 min |
| Control | 1/5 | 8.8 ± 2.4 | 9.0 ± 2.9 | 19.8 ± 9.2 | 16.0 ± 6.3 | 14.0 ± 6.3 | 11.5 ± 5.3 |
| PD-AB-SAAP | 5/5* | 9.6 ± 4.4 | 7.6 ± 5.8 | 45.8 ± 11.3# | 13.0 ± 10.3 | 38.0 ± 13.6# | 16.8 ± 9.9 |

*p < 0.05 vs Control, Fisher's Exact
p < 0.05 vs Control, ANOVA

As indicated by the data, PD-AB-SAAP increased ROSC and CPP significantly compared with standard therapy plus aortic arch epinephrine. As PD-AB-SAAP does not result in progressive volume loading, the procedure can be repeated continuously until ROSC is attained or resuscitative efforts are halted. PD-AB-SAAP may be a useful adjunctive intervention after initial SAAP therapy with a blood substitute perfusate.

EXAMPLE 3

Serial SAAP-Perflubron/Blood: Continuous SAAP versus Pulsed Diastolic SAAP

This study sought to combine all of the hypothesized beneficial elements of SAAP (aortic arch epinephrine, SAAP with perflubron, and SAAP with autologous blood as needed) and evaluate the effect on ROSC and CPP compared with a control group receiving aortic arch epinephrine. Two experimental groups were used in order to evaluate continuous SAAP infusion with CPR halted versus pulsed diastolic SAAP infusion during continued CPR.

There were three intervention groups. Animals in the control group (n=5) received standard therapy with the exception that all epinephrine doses of 0.01 mg/kg given at 3 min intervals via the aortic arch beginning at 12 min of arrest. Animals in the first experimental group (n=5) received standard therapy and aortic arch epinephrine as in the control group. In addition, they received two SAAP infusions with 300 ml of oxygenated 60% w/v perflubron emulsion beginning at 12 min and 15 min of arrest. If ROSC was not attained, autologous blood was withdrawn and reinfused at 1 min intervals beginning at 18 min of arrest.

CPR was halted during SAAP and all SAAP infusions were 50 ml bolus followed by continuous infusion [SAAP-C]. Animals in the second experimental group (n=5) received the interventions with the exception that all SAAP infusions were performed as pulsed infusions during CPR-diastole [SAAP-PD].

ROSC and CPP data obtained by these procedures are shown in Tables 2 and 3 and in FIG. 6.

due to the venous blood withdrawal occurring both prior to and during the SAAP#3 infusion. The femoral venous blood withdrawal reduced the RAP prior to SAAP#3 and limited the RAP increase during SAAP#3.

The foregoing examples are illustrative of the present invention, and are not to be construed as limiting thereof. The invention is defined by the following claims, with equivalents of the claims to be included therein.

TABLE 2

| | CPR-diastolic CPP (mmHg, mean ± S.D.) | | | | | |
|---|---|---|---|---|---|---|
| Group | ROSC | 12 min | SAAP #1 | 15 min | SAAP #2 | 18 min | SAAP #3 |
| Control | 1/5 | 7.0 ± 2.4 | 17.0 ± 11.6 | 12.4 ± 9.4 | 11.2 ± 6.4 | 8.5 ± 6.4 | 7.2 ± 5.2 |
| SAAP-C | 5/5* | 7.4 ± 4.8 | 41.2 ± 10.0# | 8.6 ± 5.3 | 39.4 ± 9.2# | 7.5 ± 2.6 | 42.2 ± 11.6# |
| SAAP-PD | 5/5* | 7.2 ± 4.8 | 43.2 ± 9.3# | 8.4 ± 4.8 | 50.8 ± 4.3 | 5.4 ± 4.3 | 58.0 ± 14.1# |

*< 0.05 vs Control, Fisher's Exact
p < 0.05 vs Control, ANOVA

TABLE 3

| Group | ROSC | Time from Initiation of CPR to ROSC with a Systolic Aortic Pressure > mmHg for 1 minute |
|---|---|---|
| SAAP-C | 5/5 | 11.9 ± 3.9 mins |
| SAAP-PD | 5/5 | 11.4 ± 4.0 mins p = NS, SAAP-PD vs SAAP-C |

These results indicate that both SAAP-C and SAAP-PD interventions can result in significantly higher rates of ROSC than the control group receiving aortic arch epinephrine. Coronary perfusion pressure (CPP) during the SAAP infusion periods was also much greater in both the SAAP-C group and the SAAP-PD group compared with the control group.

Fluoroscopy during the first SAAP infusion (SAAP#1) showed better perfusion of the coronary arteries with the SAAP infusate in the SAAP-C group than in the SAAP-PD group [perflubron is radiopaque due to the bromide it contains]. This suggests that stopping CPR during SAAP infusion may allow for a greater proportion of the SAAP perfusate to be directed to the myocardium.

CPP tended to be greater with SAAP-PD than SAAP-C in the second and third SAAP infusions (SAAP#2 and SAAP#3) which may be predominantly or at least partially related to achieving an adequate (or optimal) peripheral arterial vasoconstrictor response. Restoring peripheral arterial resistance has clearly been shown to improve the blood flow generated by closed-chest CPR. In the setting of SAAP-PD, an adequate vasoconstrictor response may increase the volume per minute of perfusion generated by the CPR sufficiently to result in a higher CPP (and overall greater liter/min perfusion) when combined with SAAP-PD than would be seen with SAAP-C alone without CPR.

Right atrial pressure (RAP) increases during the first two SAAP infusions (SAAP#1 and SAAP#2, perflubron) were similar for the SAAP-C and SAAP-PD groups. These RAP increases (a result of the intravascular volume loading during SAAP) were responsible for the progressive decreases in CPP which occurred during the SAAP#1 and SAAP#2 infusion periods. RAP increases during the third SAAP infusion (SAAP#3, autologous blood) were also similar for the SAAP-C and SAAP-PD groups. However, the magnitude of the RAP increases was less during SAAP#3 compared with SAAP#1 and SAAP#2. This was anticipated That which is claimed is:

1. An apparatus for treating a subject in cardiac arrest, comprising:
    means for perfusing the aorta of the subject with a heterologous protective solution;
    means for withdrawing autologous blood from the subject;
    means for oxygenating the autologous blood;
    means for perfusing the aorta of the subject with the oxygenated autologous blood.

2. The apparatus of claim 1, further comprising means for introducing an anticoagulant to the autologous blood.

3. The apparatus of claim 2, wherein said anticoagulant-introducing means is configured to introduce anticoagulant to autologous blood as the autologous blood enters said withdrawing means.

4. The apparatus of claim 1, further comprising means for perfusing the autologous blood in a pulsatile rhythm.

5. The apparatus of claim 1, wherein said means for perfusing with heterologous protective solution comprises a first catheter, and said means for perfusing with said autologous blood comprises said first catheter, said first catheter having an outlet configured for positioning within the aorta of said subject.

6. The apparatus of claim 5, further comprising means for oxygenating the heterologous solution prior to the perfusion of the aorta of said subject with said heterologous solution.

7. The apparatus of claim 4, wherein said withdrawing means comprises a second catheter, said second catheter extending parallel with and adjacent to said first catheter and having an outlet downstream from said outlet of said first catheter.

8. A method of treating a subject in cardiac arrest, comprising the steps of:
    blocking the descending aorta of said subject; then
    withdrawing autologous blood from said subject;
    oxygenating said autologous blood; then
    perfusing the aortic arch of said subject with an oxygenated heterologous protective solution in an amount effective to deliver oxygen to the heart of said subject; and then
    perfusing the aortic arch of said subject with oxygenated autologous blood in an amount effective to deliver oxygen to the heart of said subject.

9. The method of claim 8, wherein in said step of perfusing with heterologous protective solution, the heterologous protective solution is infused in an amount such that pulmonary oxygenation is generally unaffected.

10. The method of claim 9, wherein said withdrawing step is performed after between about 250 and 3000 milliliters of said protective solution has been infused into the aortic arch of said subject.

11. The method of claim 8, wherein said blocking step comprises the steps of:

inserting a balloon catheter into a femoral artery of said subject; then advancing said balloon catheter within the vasculature of said subject to a position within the descending aorta of said subject.

12. The method of claim 8, wherein said withdrawing step comprises withdrawing blood from a femoral vein of said subject, said femoral vein being adjacent to said femoral artery.

13. The method of claim 8, wherein said step of perfusing said aorta with protective solution comprises infusing the aorta of said subject with protective solution through a first catheter, and wherein said step of perfusing with autologous blood comprises infusing the aorta of said subject with oxygenated blood through said first catheter.

* * * * *